United States Patent
Boukhny

Patent Number: 5,808,396
Date of Patent: Sep. 15, 1998

[54] SYSTEM AND METHOD FOR TUNING AND CONTROLLING AN ULTRASONIC HANDPIECE

[75] Inventor: Mikhail Boukhny, Laguna Beach, Calif.

[73] Assignee: Alcon Laboratories, Inc., Fort Worth, Tex.

[21] Appl. No.: 769,257

[22] Filed: Dec. 18, 1996

[51] Int. Cl.$^6$ .............................. A61B 17/00; B06B 1/06
[52] U.S. Cl. ........................ 310/318; 604/22; 606/169
[58] Field of Search ................................ 310/318, 316, 310/317, 319; 604/22; 606/169; 433/88; 601/2

[56] References Cited

U.S. PATENT DOCUMENTS

| | | | |
|---|---|---|---|
| 3,964,487 | 6/1976 | Judson . | |
| 4,126,137 | 11/1978 | Archibald . | |
| 4,180,074 | 12/1979 | Murry et al. . | |
| 4,223,676 | 9/1980 | Wuchinich et al. | 606/169 X |
| 4,428,748 | 1/1984 | Peyman et al. | 604/22 |
| 4,535,759 | 8/1985 | Polk et al. . | |
| 4,639,690 | 1/1987 | Lewis | 331/96 |
| 4,642,581 | 2/1987 | Erickson | 331/154 |
| 4,703,213 | 10/1987 | Gasler | 310/316 |
| 4,808,948 | 2/1989 | Patel et al. | 331/4 |
| 4,820,152 | 4/1989 | Worrin et al. | 433/86 |
| 4,922,902 | 5/1990 | Wuchinich et al. | 606/168 X |
| 4,933,843 | 6/1990 | Scheller et al. | 604/22 X |
| 4,965,532 | 10/1990 | Sakurai | 310/316 X |
| 4,973,876 | 11/1990 | Roberts | 310/316 |
| 5,001,649 | 3/1991 | Lo et al. | 310/316 |
| 5,045,054 | 9/1991 | Hood et al. | 604/22 |
| 5,112,642 | 5/1992 | Wajid | 427/10 |
| 5,113,698 | 5/1992 | Gilj | 73/862.59 |
| 5,139,509 | 8/1992 | Fischer et al. | 606/107 |
| 5,160,317 | 11/1992 | Costin | 604/22 |
| 5,279,547 | 1/1994 | Costin | 604/22 |
| 5,331,951 | 7/1994 | Kepley | 310/316 X |
| 5,370,602 | 12/1994 | Kepley | 601/2 |
| 5,391,144 | 2/1995 | Sakurai et al. | 606/169 X |
| 5,407,525 | 4/1995 | Michel et al. | 156/627 |
| 5,421,829 | 6/1995 | Olichney et al. | 606/170 |
| 5,431,664 | 7/1995 | Ureche et al. | 606/128 |
| 5,536,272 | 7/1996 | Young et al. | 606/99 |
| 5,630,420 | 5/1997 | Vaitekunas | 128/662.03 |
| 5,676,649 | 10/1997 | Bouklay et al. | 606/169 X |
| 5,694,373 | 12/1997 | Garde | 367/135 |

FOREIGN PATENT DOCUMENTS

| | | |
|---|---|---|
| 0424686 | 5/1991 | European Pat. Off. . |
| 0586882 | 3/1994 | European Pat. Off. . |

OTHER PUBLICATIONS

*Patent Abstracts of Europe* "Circuit Arrangement for a Magnetostrictive Ultrasonic Oscillator" DE 03136028A1 Mar. 31, 1983.

Primary Examiner—Thomas P. Noland
Attorney, Agent, or Firm—Jeffrey S. Schira

[57] ABSTRACT

A system and method for tuning and controlling ultrasonic handpieces by incorporating a broad-spectrum signal as at least a component of the signal used to drive the handpiece. The response of the handpiece to this broad-spectrum signal is measured and the frequency or amplitude or both of the drive signal are adjusted in order to maintain the desired level of handpiece performance. The operation of the systems and the performance of the methods described enables the handpiece to be operated in a most effective manner over a more widely varying range of mechanical load and thermal conditions than was possible through the use of prior control systems and methods.

19 Claims, 4 Drawing Sheets

SYSTEM AND METHOD FOR TUNING AND CONTROLLING AN ULTRASONIC HANDPIECE

This invention relates to an apparatus and method for controlling an ultrasonic device and more particularly an ophthalmic phacoemulsification handpiece.

BACKGROUND OF THE INVENTION

A typical ultrasonic surgical device suitable for ophthalmic procedures consists of an ultrasonically driven handpiece, an attached hollow cutting tip, an irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece at its nodal points by relatively inflexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; and 4,922,902, the entire contents of which are incorporated herein by reference.

When used to perform phacoemulsification, the ends of the cutting tip and irrigating sleeve are inserted into a small incision of predetermined width in the cornea, sclera, or other location in the eye tissue in order to gain access to the anterior chamber of the eye. The cutting tip is ultrasonically vibrated along its longitudinal axis within the irrigating sleeve by the crystal-driven ultrasonic horn, thereby emulsifying upon contact the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the bore of the cutting tip, the horn bore, and the aspiration line and into a collection device. The aspiration of emulsified tissue is aided by a saline flushing solution or irrigant that is injected into the surgical site through the small annular gap between the inside surface of the irrigating sleeve and the outside surface of the cutting tip.

The horn assembly, including both piezoelectric and high endurance limit inert materials, used in ultrasonic handpieces must be carefully tuned for proper operation. As used herein, "tuning" refers to the process of finding and tracking the resonant frequencies of the handpiece operating under loaded or unloaded conditions. Operating the handpiece at a resonant frequency takes advantage of the crystal's energy storage capabilities, which occurs most efficiently at resonance. With proper tuning, the handpiece will store mechanical energy while operating unloaded and release this energy into the material being cut when loaded. As a consequence, for short periods of time, large amounts of energy can be directed into the material by the handpiece itself and not by the power source for the handpiece. This allows the power source to be designed to provide only the steady state power requirement of the transducer and not the loaded transients which can be many times higher.

Figure 1:
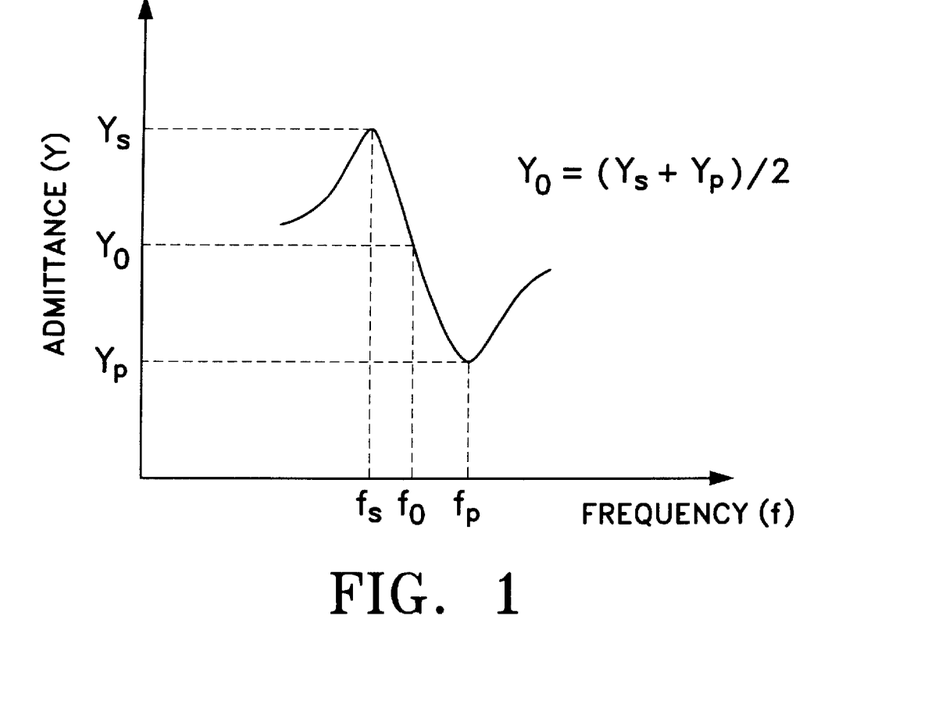
FIG. 1 is a graph of admittance versus frequency for a typical ultrasonic handpiece in the vicinity of the series and parallel resonances.

Conventional tuning and control systems determine the series and parallel resonant frequencies under a controlled loading condition, often in water, before the handpiece is subjected to loads encountered during surgery. The handpiece is excited over a range of frequencies, one frequency at a time. The response of the handpiece to each frequency, measured as the admittance (the ratio of the drive current to the drive voltage), is recorded. A typical admittance versus frequency relationship of a typical handpiece in this relatively lightly loaded pre-surgery condition is illustrated in FIG. 1. The maximum recorded admittance ($Y_s$) corresponds to the series resonance ($f_s$) and the minimum admittance ($Y_p$) corresponds to the parallel resonance ($f_p$). Driving the handpiece with a power signal at the series resonance results in the most efficient conversion of electrical to mechanical energy.

However, when the handpiece is mechanically loaded, as during surgery, the shape of the admittance versus frequency curve changes and thus the characteristic series and parallel resonant frequencies change. Curve "A" in FIG. 2 resents the characteristic admittance versus frequency curve shown in FIG. 1 for a lightly loaded handpiece. Curve "B" represents, for example, the admittance v. frequency curve when the same handpiece is mechanically loaded. As can be seen, curve "B" has shifted right ($f_{s,B} > f_{s,A}$) and the maximum admittance of curve "B" is lower Man the maximum admittance of curve "A," and the minimum admittance of curve "B" is higher than the minimum admittance of curve "A". Certain mechanical loading conditions can also shift curve "A" toward lower frequencies (to the left).

Figure 2:
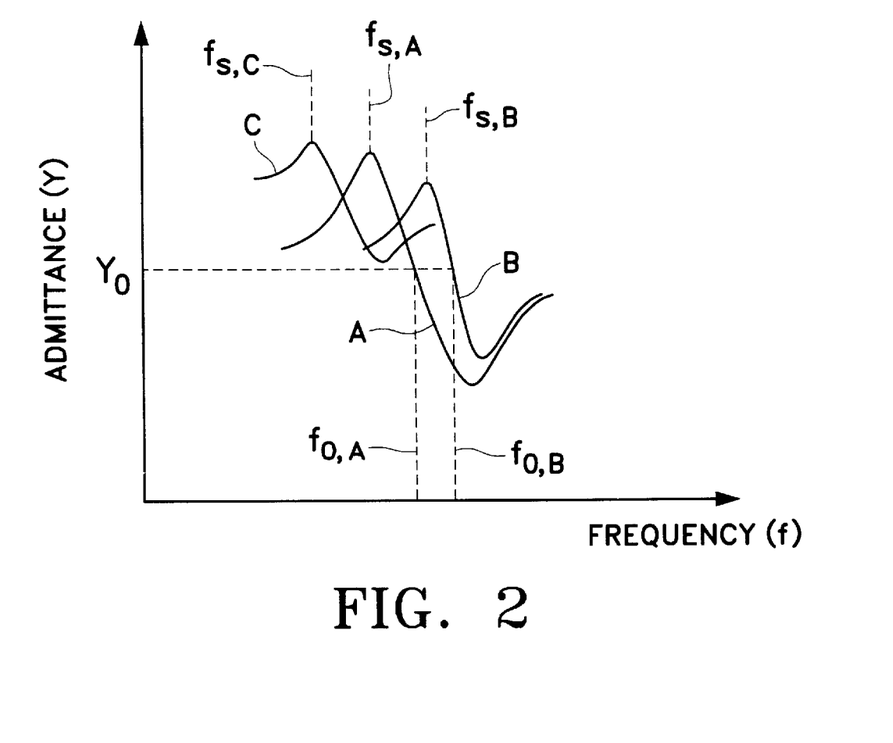
FIG. 2 a graph of admittance versus frequency illustrating the way in which the response of a typical ultrasonic handpiece may shift when the handpiece is subjected to mechanical and thermal loading.

Curve "C" represents the admittance v. frequency curve for the same handpiece when the temperature of the crystal within the handpiece has increased somewhat over room temperature. Curve "C" has shifted generally upward and leftward (i.e., higher admittance and lower frequency values) relative to curve "A." If the power signal were delivered to the handpiece at the originally determined series resonance, for example, the efficiency of the power signal drops off dramatically. Thus, subjecting the handpiece to loading without adjusting the frequency of the power signal reduces the efficiency of the power signal.

One approach to tuning a handpiece in real time during surgery employs using a power signal at a frequency that is the average of the series and parallel resonant frequencies in the relatively unloaded pre-surgery condition and adjusts the frequency of the power signal so that a constant admittance is maintained. This type of system is more fully described in U.S. Pat. No. 5,431,664 ("the '664 patent"), which is incorporated by reference. Briefly, systems of this type tune the handpiece based on a constant admittance value ($Y_0$), which is determined as the average of the maximum and minimum admittances by the equation $$Y_0 = \frac{(Y_s + Y_p)}{2}.$$

(Some commercially available constant-admittance control systems fix $Y_0$ at a point other than the average, for example, $Y_0=0.3Y_s+0.7Y_p$). As the handpiece is loaded under many types of conditions, the admittance v. frequency curve shifts along the frequency axis. Such a shift is shown, for example, by curve "A" and curve "B" in FIG. 2, with curve "B" representing a possible response of a handpiece to mass reactive loading. The control system described in the '664 patent adjusts the frequency of the drive signal to maintain the admittance at $Y_0$.

While this type of tuning and control system is effective over a relatively broad range of loading conditions, the handpiece is never operated at the series resonance and thus some efficiency is lost. Moreover, shifts in the admittance versus frequency curves along the admittance axis, such as those shown by curve "C" in FIG. 2, may render this type of constant-admittance control system ineffective. The tuning admittance ($Y_0$) is not found on any portion of curve "C," which may describe the response of a mechanically loaded and heated handpiece.

Control systems that adjust the drive frequency to coincide with the series resonance typically use phase locked loop circuits with very narrow tuning ranges. Thus, a need continues to exist for a method and control system capable of tuning an ultrasonic handpiece to its series resonance when the handpiece is subjected to widely varying load conditions.

BRIEF SUMMARY OF THE INVENTION

The present invention improves upon prior art methods of tuning and controlling ultrasonic devices by exciting the handpiece with a drive signal having a substantially constant amplitude and a broad bandwidth and analyzing the response of the handpiece to determine its series and parallel resonances. In a tuning application of the present invention, the response of the handpiece to the calibration signal is measured and analyzed by a fast fourier transform digital signal processor, which determines the series and parallel resonances of the handpiece under the pre-surgery conditions. This information is fed to an existing conventional real-time control system of the handpiece to ensure an operating frequency appropriate for that handpiece and control system. This type of tuning application is useful for any type of handpiece control system whether the handpiece is driven at a frequency that is between the series and parallel resonance (as in the constant-admittance system described in U.S. Pat. No. 5,431,664) or driven at the series resonance.

The present invention may also be used for real-time control an of ultrasonic handpiece during a surgical procedure. In a first embodiment of a control system and method of tuning and controlling a handpiece, the handpiece may be tuned before the surgical procedure begins as described in connection with the tuning embodiment of the present invention. Alteratively, the value of the series may be assumed based on the specifications of the handpiece. Once the initial value of series resonance is determined, the system applies to the handpiece a drive signal that is preferably the sum of a calibration signal and a power signal. The calibration signal has a relatively broad bandwidth and a relatively low amplitude and the power signal is at a single frequency and a sufficiently high amplitude to drive the handpiece with sufficient stroke. Preferably, the power signal would be at the series resonance. In this first control embodiment, the calibration signal encompasses a very broad range of frequencies that includes all potential values of the series resonance and thus not require independent control of it.

Only the frequency of the power signal is adjusted based on the changing response to the constant calibration signal of the handpiece under surgical conditions. The adjustment of the power signal is accomplished by, for example, a fast fourier transform digital signal processor. The processor measures the response of the handpiece to the calibration portion of the drive signal and applies proportional-integral-differential control logic to generate relevant control parameters that are incorporated into an appropriate control signal to adjust, for example, the frequency of the power signal. The proportional-integral-differential logic may be performed by the fast fourier transform digital signal processor (through appropriate programming of the processor) or by a discrete digital proportional-integral-differential control circuit.

This first control embodiment could alternatively be configured, however, such that the calibration signal has a somewhat narrower bandwidth than described above, and the center frequency of the calibration signal would be adjusted as the load on the handpiece affects its response. The adjustment to the calibration signal would be accomplished in much the same way as the adjustment to the power signal.

For both versions of this first control embodiment, the frequency of the power signal is filtered from the handpiece's response before the fast fourier transform analysis is performed. This filtering step can be accomplished by suitable programming of the fast fourier transform digital signal processor or by a notch filter between the handpiece and the digital signal processor.

In a second embodiment of a control system and method according to the present invention, the handpiece may be tuned before the surgical procedure begins as described in connection with the tuning embodiment of the present invention. Alteratively, the value of the series may be assumed based on the specifications of the handpiece. Once the initial value of series resonance is determined, the system applies to the handpiece a multifrequency drive signal having substantially constant amplitude but a narrower bandwidth than the initial calibration signal used during tuning. This broad-spectrum drive signal would be of sufficiently high amplitude to drive the handpiece with sufficient stroke (in contrast to the low amplitude calibration signal used in the initial tuning process). The bandwidth of the drive signal is narrower than that of the calibration signal used to tune the handpiece in order to avoid undesirable heating of the handpiece caused by the application of non-resonance energy. Preferably, such a drive signal would be centered approximately on the series resonance, which would maximize the efficiency of the drive signal. The bandwidth of the drive signal must also be broad enough to provide enough feedback to the control system to enable the control system to determine how the series resonance is changing. Of course, this center frequency would necessarily require adjustment as the series resonance changes to ensure that the signal remains centered approximately on the series resonance.

As in all embodiments described above, preferably a fast fourier transform digital signal processor is used to analyze the handpiece's response to the drive signal. Based on the analysis of response, the center frequency of the drive signal is adjusted so that it continually corresponds to the series resonance (although other frequencies may also be suitable). This adjustment is accomplished in much the same manner as is described above in connection with the adjustment of the frequency of the power signal in the first control embodiment.

It is accordingly an object of the present invention to provide a tuning system that quickly and accurately measures the response of an ultrasonic handpiece before the handpiece is subjected to loads during use in surgery.

It is a further object of the present invention to provide a control system and method obviating the need to perform a separate pre-surgery tuning procedure on the ultrasonic handpiece.

It is a further object of the present invention to provide a control system and method that performs real-time analysis of the frequency response of a mechanically loaded ultrasonic handpiece in order to determine at least the series resonance and in some embodiments the parallel resonance of the handpiece under mechanically loaded conditions and to adjust continuously at least the frequency of the drive signal fed to the handpiece.

Other objects, features and advantages of the present invention will become apparent with reference to the drawings, and the following description of the drawings and claims.

DETAILED DESCRIPTION OF THE INVENTION

The system and method of the present invention generally employs a broad-spectrum source to generate at least a component of the signal that drives an ultrasonic handpiece ("the drive signal"). For at least some systems according to the present invention, this broad-spectrum source is programmable and thus easily adjustable by varying certain input information fed to the source. However, other systems and methods according to the present invention may employ a fixed-spectrum source without difficulty. A fast fourier transform ("FFT") digital signal processor ("DSP") may be used to analyze the response of the handpiece to the broad-spectrum component of the drive signal. In real-time applications of the system and method of the present invention, the output of the FFT DSP is used to generate control parameters embodied within an appropriate feedback signal, which is fed to the circuitry generating the drive signal in order to alter aspects of the drive signal. The term "drive signal" as used here encompasses at least a signal useful solely for powering an ultrasonic handpiece, a signal useful solely for tuning or calibrating a handpiece, and a combination of such a power signal and such a tuning or calibration signal.

Figure 3:
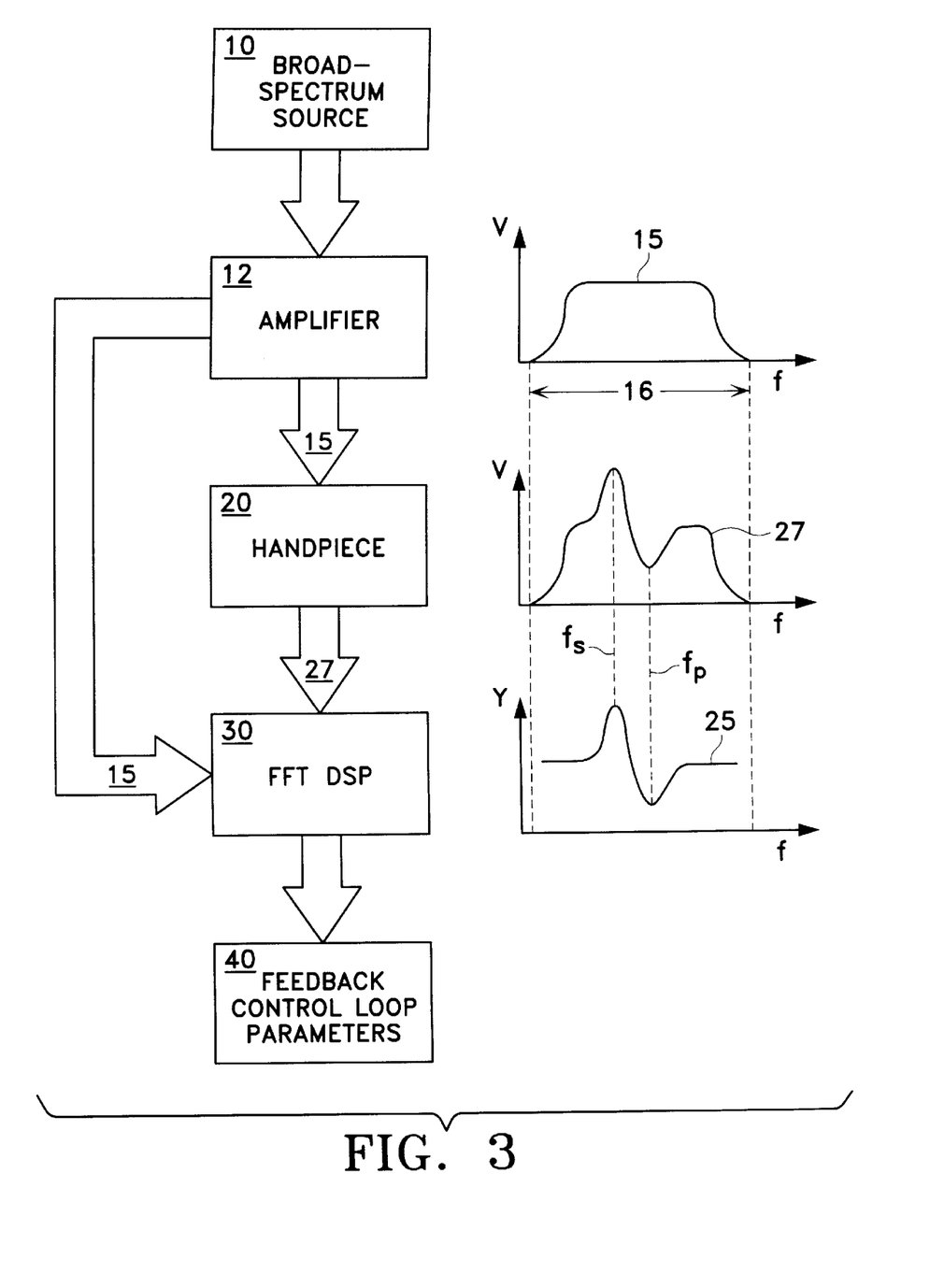
FIG. 3 is a block diagram of a system and method for tuning a handpiece before a surgical procedure according to the present invention.
Figure 4:
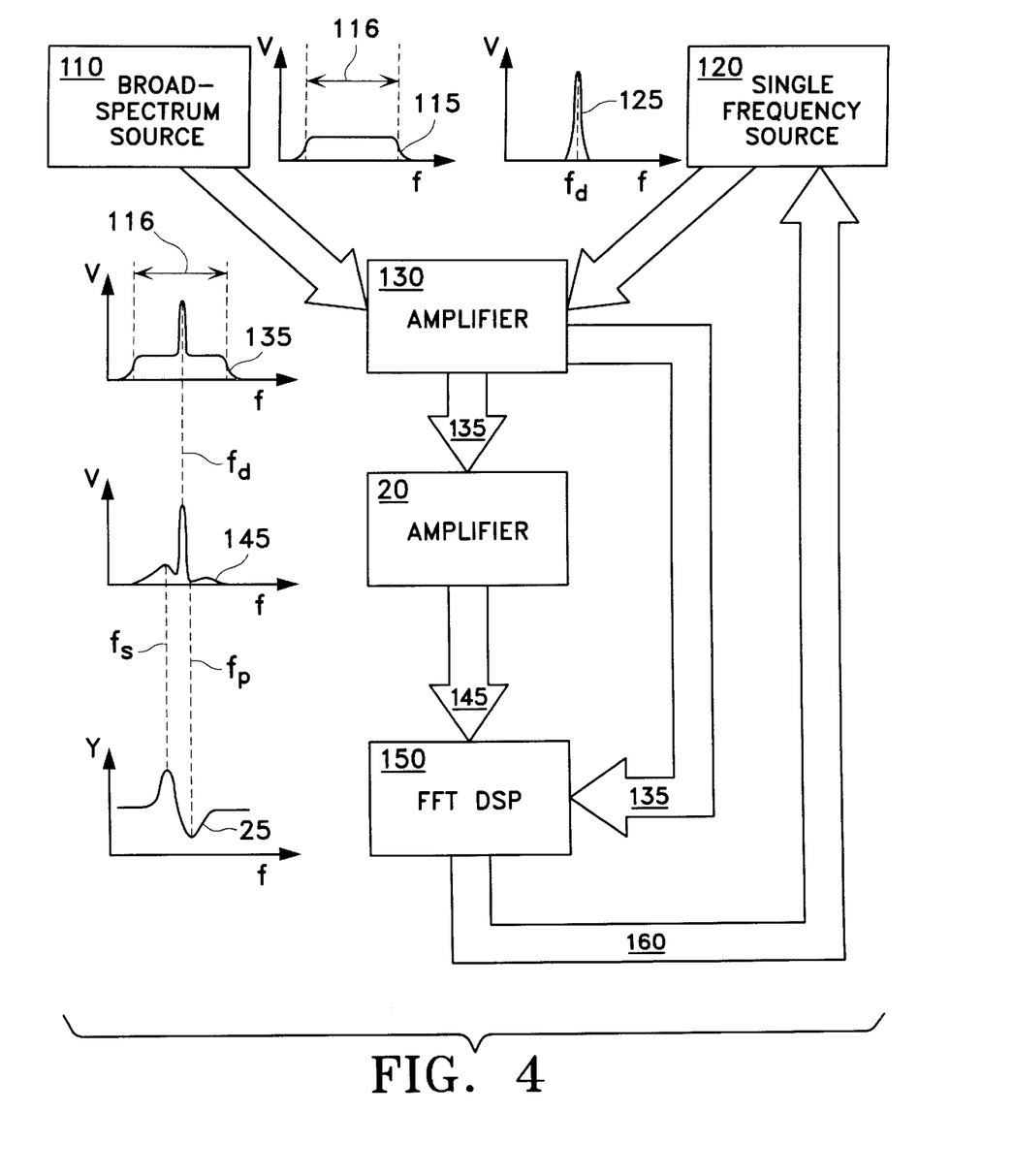
FIG. 4 is a block diagram of one embodiment of a system and method for tuning a handpiece before performing a surgical procedure and controlling the handpiece during the procedure according to the present invention.
Figure 5:
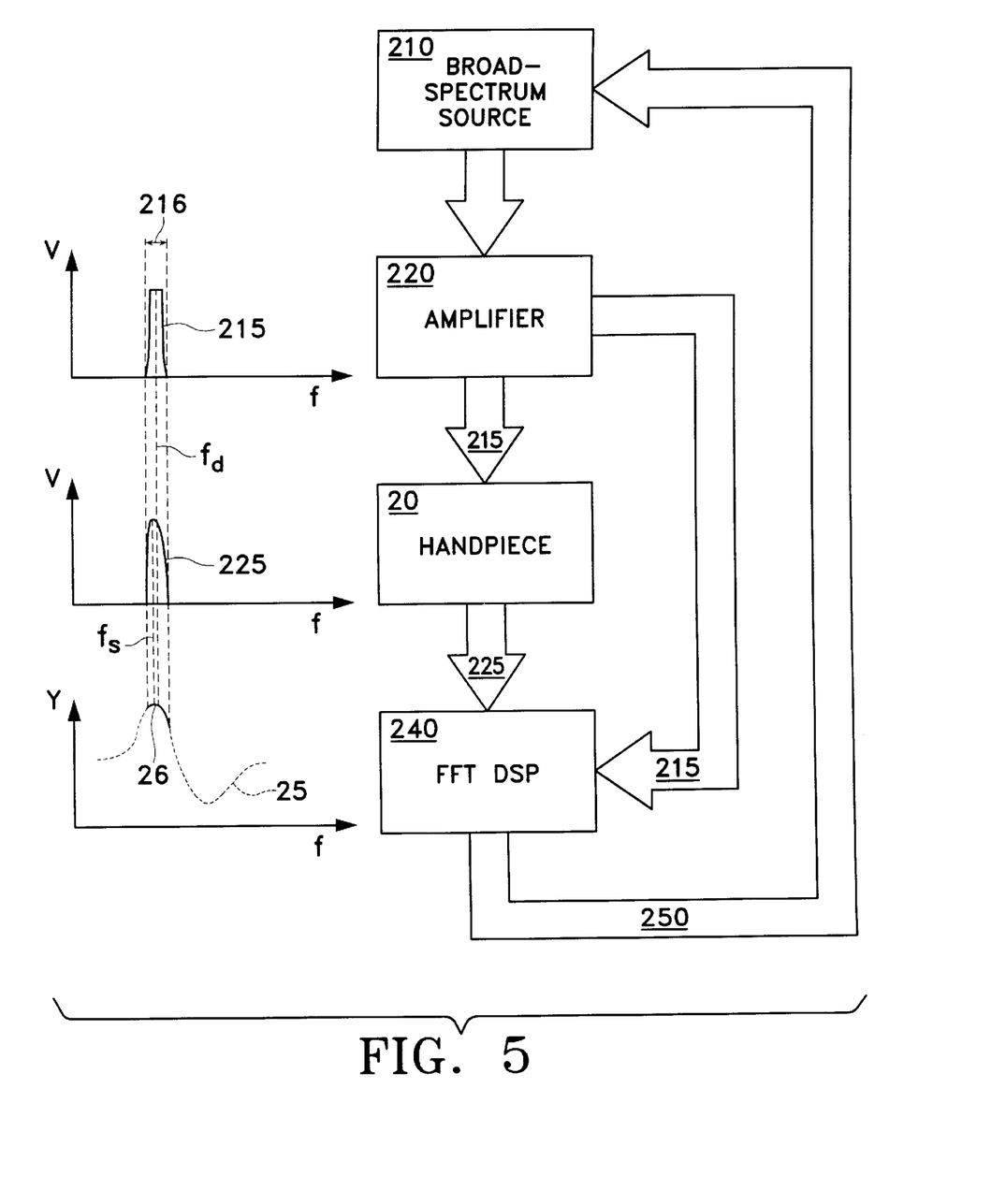
FIG. 5 is a block diagram of a second embodiment of a system and method for tuning a handpiece before performing a surgical procedure and controlling the handpiece during the procedure according to the present invention.

FIGS. 3–5 are block diagrams that illustrate three systems and methods according to the present invention for tuning and controlling an ultrasonic handpiece. FIG. 3 is a block diagram that illustrates a system and method for tuning a handpiece 20 before a surgical procedure is started. The operation of the system and performance of the method illustrated in FIG. 3 results in the determination of the characteristic response of handpiece 20 defined over a broad enough range to include the series and parallel resonances. Based on that response control parameters are generated which may be fed to the appropriate control circuitry in a conventional system for controlling handpiece 20 (which circuitry is not shown in FIG. 3).

A broad-spectrum source 10, which may be, for example, a programmable pink noise generator with an adjustable center frequency, bandwidth, and average amplitude is used in combination with an amplifier 12 to generate a drive signal 15. Drive signal 15 is preferably a signal having a bandwidth 16 that is sufficiently wide to encompass all potential values of the series and parallel resonances of handpiece 20 and a relatively constant amplitude over bandwidth 16. The bandwidth 16 of drive signal 15 may be defined as any portion of a spectrum from 25 kHz to 80 kHz, which is the operating spectrum for typical existing ultrasonic handpieces currently used in eye surgery. The inventor has found that approximately 100 Hz to 10,000 Hz is suitable as bandwidth 16 and that about 4,000 Hz is preferable. Such values of bandwidth 16 are broad enough to encompass virtually all potential values of $f_s$ and $f_p$ without being so broad that handpiece 20 is overheated by the application of non-resonance energy. Other ranges of bandwidths may be more appropriate for other ultrasonic applications, and the overall operation of the systems and methods described in this document would be equally useful for control of handpieces used in those applications.

Response signal 27 shown in FIG. 3 illustrates the actual voltage v. frequency response of handpiece 20 that is analyzed by FFT DSP 30. Admittance curve 25 is a representation of the admittance versus frequency relationship that may be exhibited by handpiece 20. After receiving drive signal 15 and response signal 27 as input (after perhaps each is attenuated to protect the input section of FFT DSP 30), FFT DSP 30 determines the shape of admittance curve 25 by calculating the ratio of response signal 27 to drive signal 15. Once admittance curve 25 is generated, FFT DSP 30 identifies series resonance $f_s$ and parallel resonance $f_p$ as the frequencies corresponding to the absolute maximum and minimum admittances respectively as shown on admittance curve 25. Based on the values of $f_s$ and $f_p$, FFT DSP 30 generates appropriate feedback control loop parameters 40 suitable for use with the existing control system (not shown). FFT DSP 30 may also identify other control parameters such as, for example, the slope of admittance curve 25 between the series and parallel resonances.

FFT DSP 30 may be a multi-purpose, programmable processor of which commercial examples are available. For example, Stanford Research Systems at 1290-D Reamwood Avenue, Sunnyvale, Calif. 94089, currently sells two FFT DSP's, the Model SR760 and Model SR770 having a single input channel. Stanford Research markets a two-channel, FFT Signal Analyzer suitable for use as FFT DSP 150, the Model SR780. All these Stanford Research FFT DSP's have real-time bandwidths of at least 100 kHz and dynamic range of 90 dB and have fully programmable center frequency, bandwidth, analysis routines, and output. All three FFT DSP's are programmed by using the interface supplied (a series of menu-driven options shown on an integral display) or by using a separate computer able to output commands over a standard RS-232 or GPIB interface. The dual-input capability of the SR780 allows it to be programmed to perform mathematical comparisons between two input signals.

Thus, FFT DSP 30 may be configured to accept response signal 27 and drive signal 15 as input and generate either an analog or digital control signal embodying control parameters 40 which are suitable for transmission to the circuitry that controls the real-time drive signal that is fed to the handpiece during a surgical procedure. The system and method illustrated in FIG. 3 is useful for all types of conventional ultrasonic handpiece control systems, whether the system is, for example, a constant-admittance type system such as that shown in the '664 patent or a system in which the drive signal is set at the series resonance of the handpiece.

FIG. 4 is a block diagram illustrating one embodiment of a control system and method for tuning and controlling an ultrasonic handpiece in real time according to the present invention. Two sources are employed to generate drive signal 135, a broad-spectrum source 110 and a single frequency source 120 (e.g., a voltage controlled oscillator). Broad-spectrum source 110 generates a calibration signal 115 having a bandwidth 116 broad enough to encompass all potential values of the series and parallel resonances ($f_s$ and $f_p$) of handpiece 20. Just as in the tuning embodiment shown in FIG. 3, bandwidth 116 could be any portion of a spectrum from about 25 kHz to 80 kHz, and a bandwidth 116 within the range of 100 Hz to 10,000 Hz is particularly suitable with about 4,000 Hz being preferable. Additionally, calibration signal 115 is of sufficiently low amplitude that it does not contribute significantly to handpiece heating. Single-frequency source 120 generates a power signal 125 having predominantly a single predetermined drive frequency $f_d$ (e.g., at the series resonance). The value of $f_d$ may be determined by tuning handpiece 20 as described in connection with FIG. 3, tuning handpiece 20 with a conventional method, or assuming the value of $f_d$ based on the specifications of handpiece 20. Additionally, power signal 125 has an amplitude substantially higher than the amplitude of calibration signal 115 and sufficiently high to effectively drive handpiece 20 under load conditions. Based on the dynamic range of current FFT DSP's, the ratio of the respective amplitudes power signal 125 and calibration signal could be as high as 90 dB. Ratios greater than 90 dB would mean that the response of handpiece 20 to calibration signal 115 would be too small to be measured by current FFT DSP's. However, a ratio of power signal 125 to calibration signal 115 of less than 10 dB would render calibration signal strong enough to drive handpiece 20 by itself, albeit in an inefficient manner because of most of the energy in such a signal would be non-resonance energy. A 20 dB to 40 dB ratio between the average amplitudes of power signal 125 and calibration signal 115 is preferable. The use of amplitude ratios within this range results in a sufficiently clean calibration signal and a high signal to noise ratio.

At least the frequency of single-frequency source 120 must be adjustable so that the control system may compensate for changes in the response of handpiece 20 caused by mechanical and thermal loading of handpiece 20. Broad-spectrum source 120 may also be programmable or otherwise adjustable so that the bandwidth, center frequency, and amplitude of calibration signal 115 may be adjusted based on appropriate input. Commercially available devices are available that are suitable for use as broad-spectrum source 110 and single-frequency source 120. Stanford Research Models SR770 and SR780 FFT Signal Analyzers include a source suitable for use as either broad-spectrum source 110 or single-frequency source 120. While the output of the SR770 or SR780 would typically require amplification to make it suitable for use as a power signal, the center frequency, bandwidth and relative amplitude of the output of this source are otherwise fully programmable.

Calibration signal 115 and power signal 125 are summed and amplified by amplifier 130 to generate drive signal 135, which is then fed to the handpiece 20. The response of handpiece 20 is shown as response signal 145, which is fed to one input channel of a two-channel FFT DSP 150 (e.g., the SR780). Drive signal 135 is fed to the other input channel of the two-channel FFT DSP 150. Drive signal 135 is fed to FFT DSP 150 rather than the sum of calibration signal 115 and power signal 125 to account for alterations in this sum introduced by amplifier 130 and inherently reflected in drive signal 135. Of course, it is possible that both drive signal 135 and response signal 145 may require attenuation before being fed to FFT DSP 150 in order to prevent damage to FFT DSP 150.

FFT DSP 150 is programmed to determine admittance curve 25 by dividing response signal 145 by drive signal 135, a task tat is easily accomplished by the Stanford Research SR780. After FFT DSP 150 determines the new value of $f_s$ (or the updated value for some other important characteristic of admittance curve 25), it may also be programmed to apply proportional-integral-differential ("PID") logic in order to generate control parameters embodied within control signal 160. Based on control signal 160, $f_d$ of single-frequency source 120 would be altered appropriately. The use of PID logic is the best way to prevent overcompensation of $f_d$ and to reduce the potential that unstable oscillations in $f_d$ are caused by the control system shown in FIG. 4. Moreover, well known control logic other than PID logic may also be used to adjust $f_d$ for changes in $f_s$ (or other parameters) depending upon the demands placed on the control system by the types of loading conditions likely encountered by handpiece 20. For example, the system may require only the use of proportional or proportional-integral control. The nature of PID and other control logic is well known in the art and thus not described further in this application.

However, the use of software implemented PID logic (within FFT DSP 150) may result in an unacceptable delay in the control system shown in FIG. 4. To avoid such delays, a special purpose, digital PID controller may be inserted in the control system at the output of FFT DSP 150. Such a digital PID controller would perform PID logic on the output of FFT DSP 150 and generate control signal 160. Such a PID controller may be any one of a number of commercially available integrated circuits or discrete components arranged in any one of many widely known configurations. Whether control signal 160 is generated by FFT DSP or a suitable digital PID controller, single-frequency source 120 preferably uses control signal 160 to adjust $f_d$ so that it corresponds to the newly discovered $f_s$ under load. The entire cycle is repeated to maintain $f_d$ at $f_s$ or another predetermined location in the characteristic response of the handpiece.

While not shown on FIG. 4, control signal 160 may also be fed to broad-spectrum source 110 in order to change one or more of the bandwidth, center frequency, or amplitude of calibration signal 115. In such an embodiment bandwidth 116 of calibration signal 115 may be significantly narrower than the fixed-bandwidth embodiment described above (having a bandwidth of approximately from 100 to 10,000 Hz and preferably about 4,000 Hz). A bandwidth suitable for use in this type of control system may be defined by the following equation: bandwidth=$A|f_s-f_p|$, where "A" has a value of between approximately 0.1 and 10 and preferably between about 1.0 and 2.0. This range of bandwidths is sufficiently broad to ensure that $f_s$ is still encompassed within response signal 145. However, the bandwidth is also sufficiently narrow to prevent undesirable heating of the handpiece caused by driving it with non-resonance energy. Essentially, in this alternative of the control embodiment shown in FIG. 4, the entire drive signal 135 rather than only power signal 125 shifts along the frequency axis and bandwidth 116 is narrower than in the control embodiment of FIG. 4 described above.

The Stanford Research SR780 contains a programmable source that is sufficiently flexible to generate drive signal 135 (for both the broad- and narrow-spectrum drive signal 135 discussed above). Thus, the SR780 is capable of being programmed to provide drive signal 135, measure response signal 145, determine admittance curve 25 and the corresponding values of $f_s$ and $f_p$ (and other control parameters as required), and generate control signal 160 in order to alter drive signal 135 to compensate for a mechanical and/or thermal load encountered by the handpiece 20 in use.

FIG. 5 is a block diagram illustrating a second embodiment of a control system and method for tuning and controlling an ultrasonic handpiece according to the present invention. Broad-spectrum source 210 in combination with amplifier 220 generates drive signal 215. Initial tuning of handpiece 20 may be accomplished as described in connection with FIG. 3. Drive signal 215 has a substantially constant amplitude over a substantially continuous spectrum of frequencies that are approximately centered on a predetermined drive frequency $f_d$. In a preferred embodiment of the invention and before handpiece 20 encounters a load of any type during surgery, $f_d$ would correspond to the series resonance $f_s$ of handpiece 20 under known conditions. The bandwidth 216 of drive signal 215 is substantially narrower than bandwidth 16 of drive signal 15 shown in FIG. 3, but bandwidth 216 is sufficiently broad to encompass the portion of the expected admittance versus frequency curve of handpiece 20 encompassing $f_s$ (values for $f_d$ other than $f_s$ may also be chosen, but choosing $f_s$ to equal $f_d$ maximizes the efficiency with which handpiece 20 uses the power delivered to it). Just as described in connection with the alternative control embodiment shown in FIG. 3, the bandwidth may be defined by the equation: bandwidth=$|f_s-f_p|$, where "A" has a value of between approximately 0.01 and 1 and preferably about 0.1.

FFT DSP 240 generates control signal 250 and FFT DSP 150 shown in FIG. 4 generates control signal 160 in a substantially similar manner. When, for example, a mechanical load is applied to handpiece 20 or when handpiece 20 warms somewhat above room temperature, response signal 225 of handpiece 20 may shift toward lower frequencies as shown in FIG. 5. That is, $f_s$ is less than $f_d$ even though the two were equal before any load was encountered by handpiece 20. The corresponding portion 26 of admittance curve 25 would be calculated by FFT DSP 240 as the ratio of response signal 225 to drive signal 215. Once portion 26 of admittance curve 25 is determined, FFT DSP 240 finds the new value of $f_s$ that corresponds to the maximum admittance in portion 26.

If $f_s$ has shifted so far that it no longer is present within portion 26 of admittance curve 25, then the slope of portion 26 could be used to determine the probable value of $f_s$. A positive slope of portion 26 over its entire range would likely indicate that $f_s$ is greater than the highest frequency present in portion 26 of admittance curve 25. A negative slope of portion 26 over its entire range would likely indicate that $f_s$ is less than the lowest frequency present in portion 26.

Whether $f_s$ is located within portion 26 of admittance curve 25 or not, PID logic is used to temper the way in which $f_d$ is adjusted. The application of PID logic in the control system shown in FIG. 5 is substantially the same as that described in connection with the system shown in FIG. 4. The PID logic may be implemented by either FFT DSP 240 or in a separate, special purpose, digital PID circuit (not shown).

While certain embodiments of the present invention have been described above, these descriptions are given for purposes of illustration and explanation. Variations, changes, modifications and departures from the systems and methods disclosed above may be adopted without departure from the scope or spirit of the present invention which, in sum, employs a broad-spectrum source to supply at least a component of the drive signal for an ultrasonic handpiece and uses the response of the handpiece to that drive signal as a means of tuning the handpiece or compensating for changes in the operating characteristics of the handpiece while in use or both.

I claim:

1. A method of tuning an ultrasonic device comprising a handpiece, comprising the steps of:
   a) generating a drive signal over a substantially continuous spectrum of frequencies from a low frequency below a predetermined drive frequency to a high frequency above the drive frequency;
   b) exciting the handpiece with the drive signal;
   c) measuring a response signal generated by the handpiece in response to the exciting step;
   d) comparing the drive signal to the response signal in order to determine an admittance versus frequency relationship over the spectrum of frequencies;
   e) determining at least one control parameter based on the shape of the response signal; and
   f) generating a control signal containing information about the control parameter.

2. The method of claim 1, further comprising the step of controlling the ultrasonic device by adjusting the drive frequency based on the control parameter.

3. The method of claim 2, in which the controlling step comprises adjusting the drive frequency such that it is substantially equal to a series resonance of the handpiece.

4. The method of claim 2, in which the drive signal further comprises:
   a) a power component at substantially the drive frequency and having an average power amplitude; and
   b) a calibration component over the spectrum of frequencies and having an average calibration amplitude that is substantially constant over the spectrum of frequencies and significantly lower than the average power amplitude.

5. The method of claim 4, in which the controlling step comprises adjusting the drive frequency such that it is substantially equal to a series resonance of the handpiece.

6. The method of claim 5, in which the difference between the power amplitude and the calibration amplitude is from approximately 10 dB to 90 dB.

7. The method of claim 6, in which the difference between the power amplitude and the calibration amplitude is from approximately 20 dB to 40 dB.

8. The method of claim 7, in which the difference between the high frequency and the low frequency is between approximately 100 Hz and 10,000 Hz.

9. The method of claim 8, in which the difference between the high frequency and the low frequency is approximately 4,000 Hz.

10. The method of claim 4, further comprising the step of adjusting the low frequency and the high frequency such that a ratio of the difference between the drive frequency and the low frequency to the difference between the high frequency and the low frequency remains approximately constant.

11. The method of claim 10, in which the controlling step comprises adjusting the drive frequency such that it is substantially equal to a series resonance of the handpiece.

12. The method of claim 11, in which the difference between the power amplitude and the calibration amplitude is from approximately 10 dB to 90 dB.

13. The method of claim 12, in which the difference between the power amplitude and the calibration amplitude is from approximately 20 dB to 40 dB.

14. The method of claim 13, in which the difference between the high frequency and the low frequency is approximately equal to a range from 0.1 to 10.0 times the difference between a parallel resonance and a series resonance of the handpiece.

15. The method of claim 14, in which the difference between the high frequency and the low frequency is approximately between 1.0 and 2.0 times the difference between a parallel resonance and a series resonance of the handpiece.

16. The method of claim 2, further comprising the step of adjusting the low frequency and the high frequency such that a ratio of the difference between the drive frequency and the low frequency to the difference between the high frequency and the low frequency remains approximately constant.

17. The method of claim 16, in which the controlling step comprises adjusting the drive frequency such that it is substantially equal to a series resonance of the handpiece.

18. The method of claim 17, in which the difference between the high frequency and the low frequency is approximately equal to a range from 0.01 to 1 times the difference between a parallel resonance and a series resonance of the handpiece.

19. The method of claim 18, in which the difference between the high frequency and the low frequency is approximately 0.1 times the difference between a parallel resonance and a series resonance of the handpiece.

* * * * *